(12) United States Patent
Paes

(10) Patent No.: US 9,504,403 B2
(45) Date of Patent: Nov. 29, 2016

(54) NERVE SENSING/MONITORING DEVICE

(75) Inventor: Roel Paes, Maastricht (NL)

(73) Assignee: THE MAGSTIM COMPANY LIMITED, Carmarthenshire (GB)

( * ) Notice: Subject to any disclaimer, the term of this patent is extended or adjusted under 35 U.S.C. 154(b) by 314 days.

(21) Appl. No.: 14/343,540

(22) PCT Filed: Sep. 7, 2012

(86) PCT No.: PCT/GB2012/052205
§ 371 (c)(1),
(2), (4) Date: Jul. 7, 2014

(87) PCT Pub. No.: WO2013/034923
PCT Pub. Date: Mar. 14, 2013

(65) Prior Publication Data
US 2014/0330101 A1    Nov. 6, 2014

(30) Foreign Application Priority Data

Sep. 9, 2011 (GB) .................................. 1115625.4

(51) Int. Cl.
| | | |
|---|---|---|
| *A61B 5/0492* | (2006.01) | |
| *A61B 5/04* | (2006.01) | |
| *A61B 5/042* | (2006.01) | |

(Continued)

(52) U.S. Cl.
CPC ......... *A61B 5/0492* (2013.01); *A61B 5/04001* (2013.01); *A61B 5/0421* (2013.01); *A61B 5/0488* (2013.01); *A61B 5/4893* (2013.01); *A61B 5/6847* (2013.01); *A61B 5/6879* (2013.01)

(58) Field of Classification Search
CPC .............. A61B 5/0492; A61B 5/0421; A61B 5/04001

USPC ........................................................ 600/380
See application file for complete search history.

(56) References Cited

U.S. PATENT DOCUMENTS

| | | |
|---|---|---|
| 4,090,518 A | 5/1978 | Elam |
| 4,567,882 A | 2/1986 | Heller |
| 4,960,122 A | 10/1990 | Mizus |

(Continued)

FOREIGN PATENT DOCUMENTS

| | | |
|---|---|---|
| WO | 9324170 A1 | 12/1993 |
| WO | 2011041690 A1 | 4/2011 |

OTHER PUBLICATIONS

International Search Report dated Nov. 26, 2012.

(Continued)

*Primary Examiner* — Lee S Cohen
(74) *Attorney, Agent, or Firm* — Troutman Sanders LLP; Ryan A. Schneider; Chris N. Davis

(57) ABSTRACT

Sensor arrangement for sensing activity in a nerve or muscle, the sensor arrangement being arranged to be secured to an insertion member for insertion into a body cavity, the sensor arrangement (2) comprising a support for supporting one or more sensing elements, the support comprising a first zone (10a) and a second zone (10b) spaced apart longitudinally from the first zone, where each of the first and second zones are arranged to be secured to the insertion member to define a fixed spacing therebetween, wherein a plurality of strips (16) comprising one or more sensing elements bridge at least part of the spacing between the first and second zones, the strips being moveable laterally relative to the longitudinal length of the support.

19 Claims, 3 Drawing Sheets

(51) Int. Cl.
*A61B 5/0488* (2006.01)
*A61B 5/00* (2006.01)

(56) References Cited

U.S. PATENT DOCUMENTS

| | | | |
|---|---|---|---|
| 4,976,261 | A | 12/1990 | Gluck et al. |
| 5,016,647 | A | 5/1991 | Sanders |
| 5,125,406 | A | 6/1992 | Goldstone et al. |
| 5,135,001 | A | 8/1992 | Sinofsky et al. |
| 5,178,145 | A | 1/1993 | Rea |
| 5,343,860 | A | 9/1994 | Metzger et al. |
| 5,499,625 | A | 3/1996 | Frass et al. |
| 6,161,537 | A | 12/2000 | Gravenstein et al. |
| 6,173,199 | B1 | 1/2001 | Gabriel |
| 6,216,696 | B1 | 4/2001 | van den Berg |
| 6,266,548 | B1 | 7/2001 | Lamade et al. |
| 6,292,701 | B1 | 9/2001 | Prass et al. |
| 6,334,068 | B1 | 12/2001 | Hacker |
| 6,651,665 | B1 | 11/2003 | Sellers et al. |
| 6,701,918 | B2 | 3/2004 | Fariss et al. |
| 6,715,491 | B2 | 4/2004 | Cooper et al. |
| 6,735,471 | B2 | 5/2004 | Hill et al. |
| 7,198,635 | B2 | 4/2007 | Danek et al. |
| 7,216,001 | B2 | 5/2007 | Hacker et al. |
| 7,543,586 | B2 | 6/2009 | Qureshi et al. |
| RE41,334 | E | 5/2010 | Beatty et al. |
| 2005/0085743 | A1 | 4/2005 | Hacker et al. |
| 2006/0009690 | A1 | 1/2006 | Fuimaono et al. |
| 2006/0147492 | A1 | 7/2006 | Hunter et al. |
| 2006/0190053 | A1 | 8/2006 | Dobak, III |
| 2007/0016097 | A1 | 1/2007 | Farquhar et al. |
| 2007/0073160 | A1 | 3/2007 | Imam |
| 2007/0137652 | A1 | 6/2007 | Qureshi et al. |
| 2007/0156041 | A1 | 7/2007 | Rea |
| 2010/0179417 | A1 | 7/2010 | Russo |
| 2010/0317956 | A1 | 12/2010 | Kartush |
| 2011/0245647 | A1* | 10/2011 | Stanislaus .......... A61B 1/00082 600/380 |

OTHER PUBLICATIONS

International Search Report dated Jul. 30, 2008.
European Search Report dated Aug. 27, 2010.
European Office Action dated Dec. 11, 2013.
Kartush, et al., "Electroneurography and Intraoperative Facial Monitoring in Contemporary Neurotology," Otolaryngology—Head and Neck Surgery, vol. 101. No. 4, pp. 496-503, Oct. 1989.
Kartush. et al., "Facial Nerve Testing; ENoG and Interaoperative Monitoring," J. Johnson (ed.), Mosby, 1988.
Kartush,. et al., "Intraoperative Facial Nerve Monitoring: A Comparison of Stimulating Electrodes," Laryngoscope, vol. 95, pp. 1536-1540, Dec. 1985.
Kartush,. et al., "Facial Nerve Outcome in Acoustic Neuroma Surgery," Otolaryngologic Clinics of North America, vol. 25, No. 3, pp. 623-647, Jun. 1992.
Kartush,. et al., "Intraoperative Facial Nerve Monitoring," Otology, Neurotology and Skull Base Surgery, Neuromonitoring in Otology and Head and Neck Surgery, Raven Press, New York, ch. 5, pp. 99-120, 1992.
Kartush, et al., "Acoustic Neuroma Update," Otolaryngologic Clinics of North America, Philadelphia, vol. 29, No. 3, Jun. 1996.
Witt, Robert L., Recurrent Laryngeal Nerve Electrophysiologic Monitoring in Thyroid Surgery: The Standard of Care?, Journal of Voice, vol. 19, Issue 3, pp. 497-500, Sep. 2005.
Kartush, et al., "Facial Electroneurography: Clinical and Experimental Investigations: Otolaryngology—Head and Neck Surgery," vol. 93, No. 5, pp. 516-523, Aug. 1985.

* cited by examiner

NERVE SENSING/MONITORING DEVICE

CROSS-REFERENCE TO RELATED PATENT APPLICATIONS

This application is a U.S. National Stage Application of, and claims the benefit pursuant to 35 U.S.C. §371 of International Patent Application Serial No. PCT/GB2012/052205, filed on Sep. 7, 2012, which claims priority to and the benefit of Great Britain Application No. 1115625.4, filed on Sep. 9, 2011, both which are incorporated herein in their entirety by reference.

The present invention relates to nerve/muscle monitoring, and more particularly to a sensor arrangement or device to facilitate nerve/muscle sensing or monitoring.

A risk presented by any surgery, and as described below thyroid surgery, parathyroid surgery, skull base surgery, cervical spine, or any other surgery in the space around the oropharynx, larynx, trachea or oesophagus, is damage to the Recurrent Laryngeal Nerves ("RLN"). RLNs control the vocal cords, and damage to them can result in full or partial vocal cord paralysis. An issue with RLNs is that they are small and difficult to identify, particularly where surrounding tissue is bloodied, inflamed or otherwise disrupted due to surgery or trauma. Another issue is that simply trying to identify RLNs by touch can stretch or tear those nerves, which can result in hoarseness, difficulty in speech, aspiration of food or liquids (which can result in pneumonia), and life-threatening airway obstruction. There are similar issues associated with other surgery types in other parts of a body where nerves may potentially be damaged.

There have been recent efforts when considering avoiding damage to RLNs to use intraoperative RLN monitoring techniques, with the objective of reducing the risk of damage to the RLNs and subsequent vocal cord impairment or paralysis. One advocated form of RLN monitoring implements electromyography (EMG) to protect the nerves.

A common procedure in which laryngeal EMG is used is a thyroid surgery. In this procedure, a specialized endotracheal tube (ET tube) is placed through the patient's nose or mouth and into the trachea to assist in respiratory ventilation and/or to provide anaesthesia.

The ET tube also passes between the sets of laryngeal muscles, and typically rests adjacent the left and right posterior cricoarytenoid muscles. The specialized ET tube includes a pair of exposed, cylindrical wires on its external surface or embedded therein. These wires form electrodes that are intended to contact the various vocal muscles when the ET tube is (a) properly inserted at the correct depth, and (b) properly rotationally oriented relative to the trachea and larynx. These electrodes of the ET tube are capable of detecting EMG signals generated by an electrical probe. An example of such a specialized tube is disclosed in U.S. Pat. No. 5,125,406.

During the procedure, a surgeon applies the electrical probe to the area in which he believes the RLN is located. If the electrical probe applies voltage to or near the RLN, the electrical pulse is carried to the vocal muscles (primarily the "thyroarytenoid muscles" along the vocal cords anteriorly and the "posterior cricoarytenoid muscles" posteriorly) through the RLN, which in turn causes contraction of the vocal muscles which generate their own electric pulse. The respective wire electrode on the ET tube facing the stimulated vocal muscles subsequently detects the electromyographic (EMG) response. The detecting electrode transfers a signal to a receiver or EMG monitor, which emits an audio or visual alarm. This output alerts the surgeon that the probe is close to the RLN so that the surgeon can confirm the nerve's location and minimize trauma in the probed location.

Known sensors have significant limitations. They are either too rigid resulting in poor contact being achieved with the nerves thus producing poor quality output for the surgeon to determine the nerve's location. Furthermore, such a rigid sensor may result in damage to the nerve. Other concepts include expandable sensors which may expand in contact with fluid, however there may be difficulties associated with insertion and removal. Other arrangements contemplate complex actuation mechanisms for expanding the sensor, however this has the potential of causing damage to a patient through excessive force applied, and adds significant complexity to the sensor/insertion member arrangement, also requiring a practitioner to take an additional step when inserting into a patient.

The present invention overcomes at least the above-mentioned problems.

According to an aspect of the present invention there is a sensor arrangement for sensing activity in a nerve or muscle, the sensor arrangement being arranged to be secured to an insertion member for insertion into a body cavity, the sensor arrangement comprising a support for supporting one or more sensing elements, the support comprising a first zone and a second zone spaced apart longitudinally from the first zone, where each of the first and second zones are arranged to be secured to the insertion member to define a fixed spacing therebetween, wherein a plurality of strips comprising one or more sensing elements bridge at least part of the spacing between the first and second zones, the strips being moveable laterally relative to the longitudinal length of the support.

The present invention provides significant benefits over the prior art. Importantly, the strips bridge the separation longitudinally between a part of the first and second zone that is secured to an insertion member such as a cannula. This is beneficial as the strips which include a sensing element such as an electrode are flexible meaning that they have movement radially away from the insertion member. Accordingly, during insertion or removal of the insertion member, the strips will not cause damage to a patient.

Furthermore, there is the significant benefit that the strips may move radially outwardly which ensures positive contact with an adjacent nerve. This movement however is not forced as would happen if the strips were for example mechanically actuated, which again has the potential to cause damage to the nerves that the device is aiming to be used to protect. This is achieved by ensuring securing of the first and second zones onto the underlying insertion member. The strips are therefore reactive to their surroundings. They do not require third party manipulation once secured to the insertion member.

Additionally, rotation of the insertion member does not cause disassociation of the sensing element from the nerve to be sensed, as another strip including a sensing element will take over contact with the adjacent tissue. Another significant benefit is that the 'at rest' configuration of the strips means that the strips are expanded or project outwardly laterally with respect to the longitudinal length of the sensor arrangement. This ensures good compliance with the shape of the internal cavity of a patient, but also enables deflection of the strips with minimal force to a non-expanded configuration during insertion or in-situ depending on the internal cavity into which the sensor arrangement is sited. Again, there is no actuator forcing the strips apart, reducing complexity and chance of causing damage to the nerve.

The sensing element preferably comprises an electrode. The electrode is beneficially a conductive ink, preferably including silver.

The strips extending between the first and second zone are preferably unsecured intermediate the first and second zone. The strips are beneficially independently moveable to one another. It is noted that movement of one strip has no influence on the movement of other strips. This enables a single strip to move and deflect to correspond to the shape of the internal cavity in which the sensor arrangement is inserted without another strip such as an adjacent strip having to move. This ensures that the sensor arrangement complies or corresponds to the internal shape of the body cavity without causing potential damage to the wall of the cavity, the nerve or any other tissue.

The support preferably comprises an intermediate portion arranged to extend between the first and second zones. Thus, the intermediate portion fixes separation between the first and second zones. This is particularly beneficial when the medical practitioner wishes to secure the sensor arrangement to an insertion element such as a cannula. This means that ease of position of the sensor arrangement onto the cannula is achieved and it is not left to the medical practitioner to judge the separation between the first and second zones.

The intermediate portion of the support is preferably arranged to be secured to an insertion member.

The sensing element support beneficially comprises the one or more strips for supporting the one or more sensing elements. Accordingly, it is beneficial that the sensing element(s) is carried by the sensing element support, as shown in the exemplary embodiments. The sensing element(s) may be embedded into or printed onto the sensing element support and in particular the one or more strips. Part of the sensing elements may be coated thereby insulating part of the sensing element from acting as an electrode.

The strips beneficially extend substantially parallel to each other.

The strips are preferably spaced apart. The spacing may be achieved by a slit, or may be larger to comprise a slot or elongate aperture.

A securing arrangement is preferably provided for securing the first zone and a securing arrangement for securing the second zone to the insertion member. The securing arrangement is preferably an adhesive, and even more preferably a double sided adhesive. The adhesive material may be cut into strips and one face secured to the sensing element support, and one face subsequently secured to the insertion member. A backing cover is beneficially provided adhered to the adhesive material that may be removed prior to adhesion to an insertion member.

At least one of the securing arrangements preferably extends substantially transversely to the longitudinal length of the strips.

At least one of the securing arrangements preferably extends adjacent a transverse edge of the sensing element support.

The strips are beneficially flexible and are moveable radially outwardly from the insertion member when the sensor arrangement is secured to an insertion member.

The intermediate portion of the support preferably comprises a securing arrangement for securing the intermediate zone to an insertion member. The securing arrangement preferably comprises an adhesive, and even more preferably is combined with the adhesive material for securing the first and second zones.

The support is preferably arranged to conform to the outer surface configuration of an insertion member. The support is therefore arranged to flex and to bend to accommodate the outer surface configuration of an insertion member. The support preferably comprises at least one tab element projecting generally transversely to the longitudinal length of the strips (and preferably at least two tabs). Such tab(s) are provided to aid in location on an insertion member such as a cannula as these tabs can be positioned first onto the insertion member by a medical practitioner which ensures substantially parallel alignment of the strips with the longitudinal length of the insertion member.

Also according to the present invention, there is a laryngeal sensor arrangement as hereinbefore described with respect to a generic sensor arrangement.

The present invention extends to an insertion member comprising an elongate body having a sensor arrangement as hereinbefore described secured to the elongate body. The sensor arrangement is preferably wrapped around the body. The strips of the sensor arrangement preferably substantially align parallel to the longitudinal length of the elongate body.

The spacing between the first and second zones is preferably fixed when the sensor is secured to an insertion member. This means that the sensor will not become unintentionally extended or contracted resulting in possible danger to the patient or loss in effectiveness of the sensing of a nerve or muscle.

The electrode preferably comprises a conductive ink, preferably printed onto the sensing element support including the strips, and preferably including silver.

The insertion member may have an elongate body and the sensor is preferably wrapped around the elongate body.

The insertion member may be a cannula.

According to another aspect of the present invention there is a sensor arrangement for sensing activity in a nerve or muscle, the sensor arrangement being arranged to be secured to an insertion member for insertion into a body cavity, the sensor arrangement comprising a support having a longitudinal length and a plurality of sensing element strips extending in the longitudinal length of the support, the sensing element strips comprising a first portion and a second portion and an intermediate portion extending therebetween, the strips arranged to conform to the geometry of a body cavity, the strips secured to the support at the first and second portions, wherein the intermediate portion is moveable laterally to the support, and wherein the support spans the separation between the first and second portions and said span is fixed in length.

According to another aspect of the present invention there is a sensor for sensing activity in a nerve or muscle, the sensor being arranged to be secured to an insertion member for insertion into a body cavity, the sensor comprising a sensing element support for supporting one or more sensing elements, the sensing element support comprising a first zone and a second zone spaced apart from the first zone, where the first and second zones are arranged to be secured to the insertion member, wherein a plurality of strips bridge at least part of the spacing between the first and second zones, wherein the strips comprise one or more sensing elements.

The present invention will now be described by way of example only with reference to the accompanying drawings where:

Figure 4A:
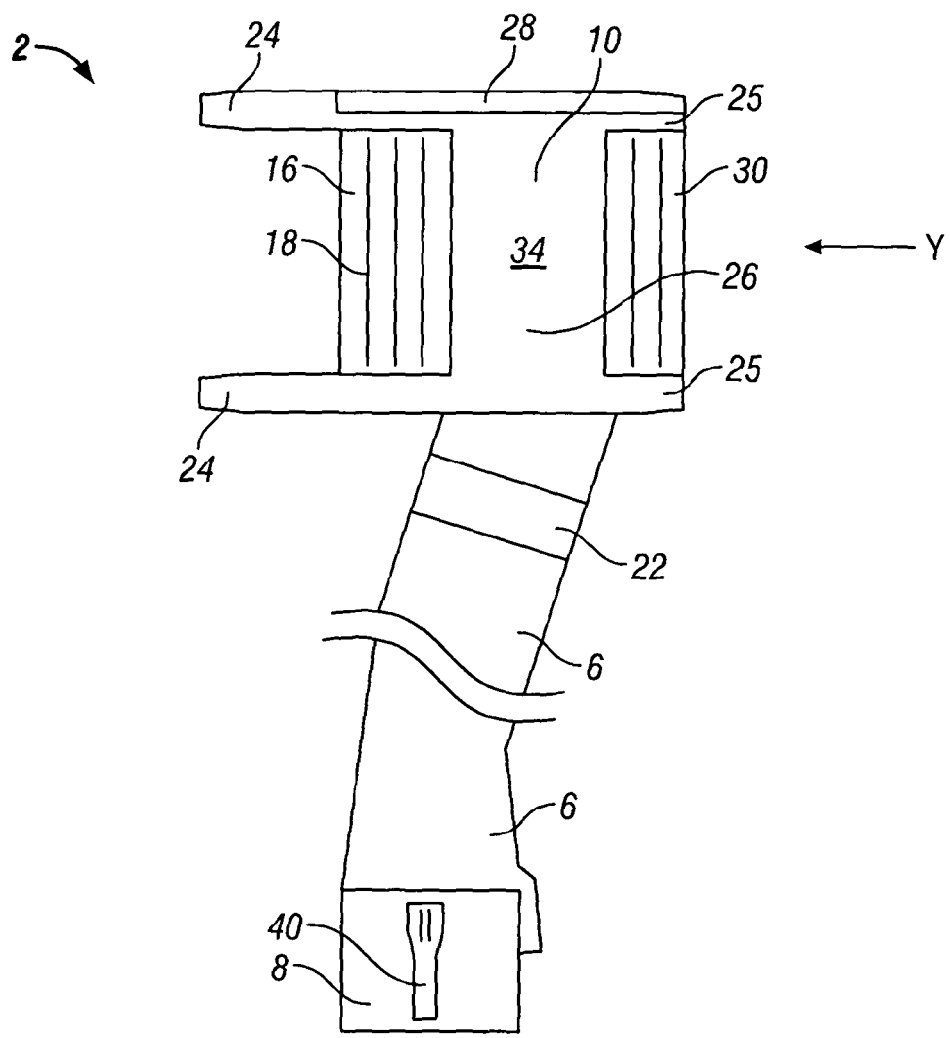
Figure 4B:
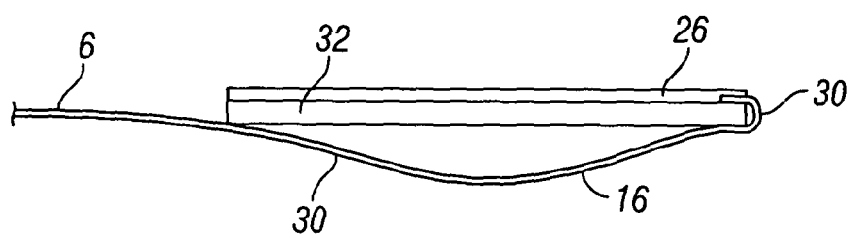
Figure 4C:
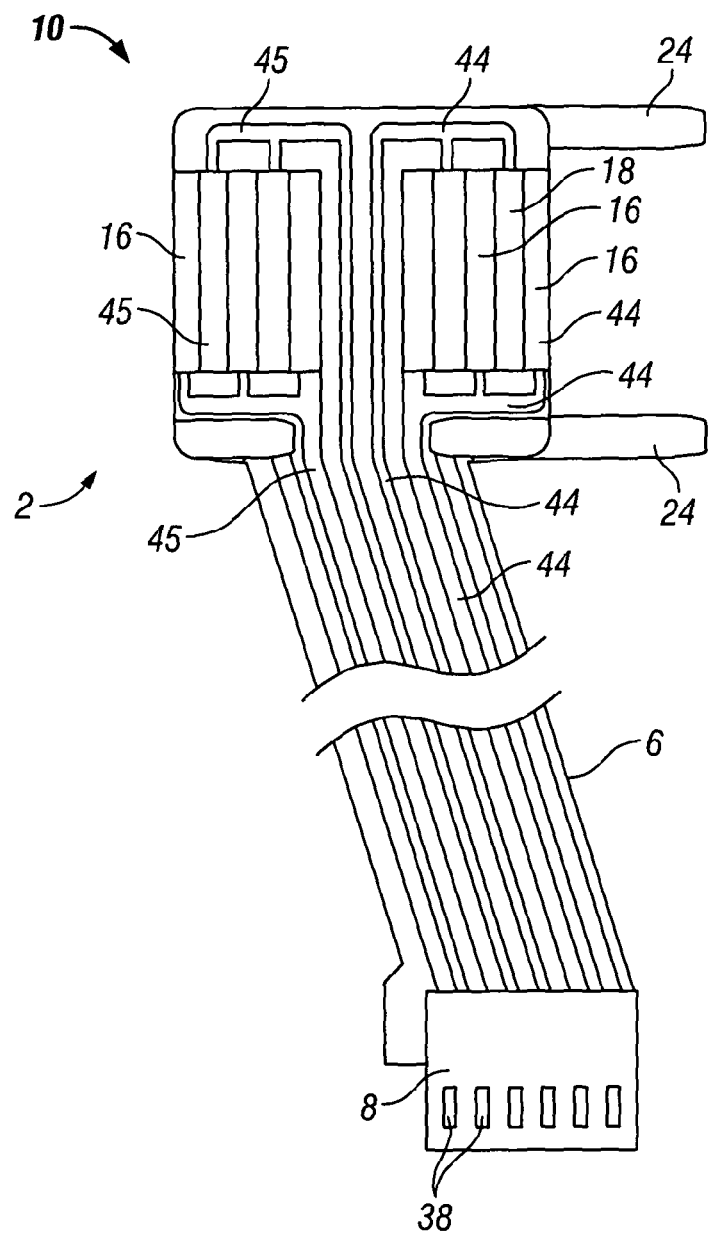

FIG. 4a-c is a schematic bottom plan view, side view and plan top view respectively of a sensor arrangement according to a preferred embodiment of the present invention (not secured to an insertion member).

Figure 1:
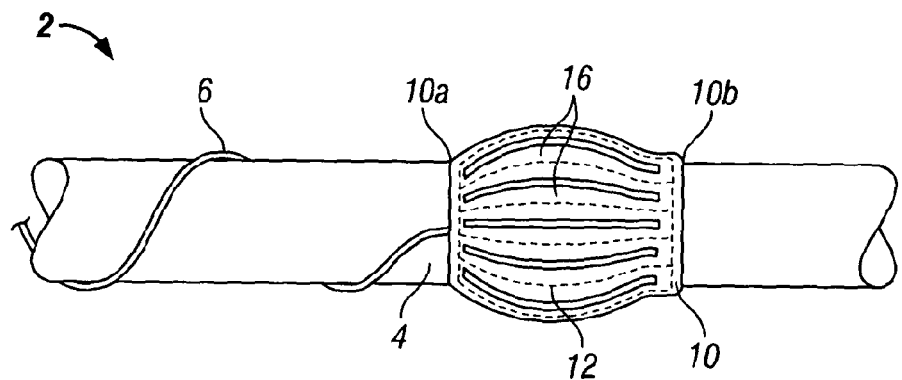
FIG. 1 is a schematic perspective view of a nerve sensing/monitoring sensor sited on a tube such as a cannula according to an exemplary embodiment of the present invention.
Figure 2:
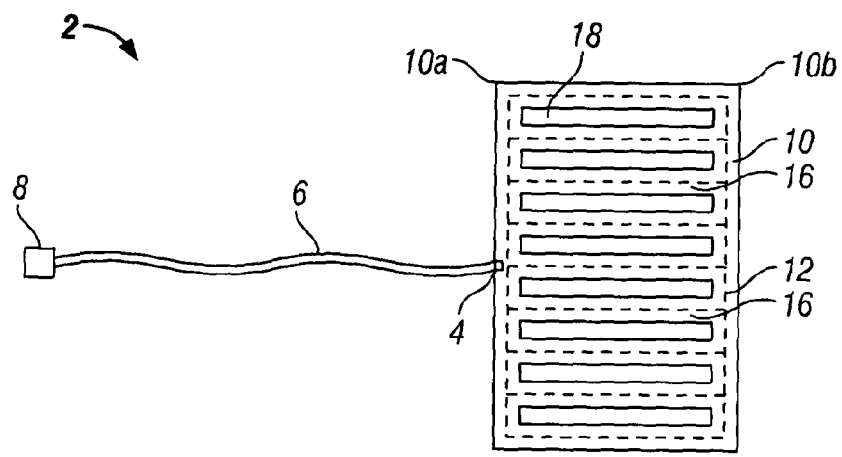
FIG. 2 is a schematic plan view of the upper or outer side of a nerve sensing/monitoring sensor according an exemplary embodiment of the present invention.

Referring to FIG. 1, there is a nerve monitoring sensor arrangement 2 which is arranged to detect nerve and/or muscle activity. The sensor arrangement 2, when prepared for use as shown in FIG. 1, is secured to a conduit, pipe or insertion member such a cannula for insertion into a body cavity. The sensor arrangement includes a signal output port 4 and a conducting filament 6 extends to a nerve monitoring device (not shown). An output element 8 is provided for connection to a nerve monitoring device.

In use, a probe is provided in communication with the output element 8 and is engaged by a surgeon at a location where a target nerve such a recurrent laryngeal nerve is suspected to be located. The probe provides an electrical impulse which in turn is transmitted through the target nerve to an associated target muscle such as a laryngeal muscle and/or the vocal cords. The subsequent activity of the target muscle is sensed by the sensor 2 and the signal is output to the output element 8. The signal is received by a nerve monitoring device which provides information to the surgeon on the location of the target nerve relative to the probe. Accordingly, if, for example, a surgeon is removing a tumour through which a nerve runs, then the surgeon can determine how close they may be to the tumour during its removal and thus avoid damaging the vocal cords.

It should be appreciated to the skilled addressee that although the embodiments herein are described with respect to the laryngeal space, nerves in any internal body space can be monitored using the device of the present invention. For example, the present invention can be used in prostrate, abdominal, pelvic or rectal surgery. Furthermore, the device can be used to locate nerves that are to be rendered inoperative or to be used for acute or chronic neural stimulation.

Reference is made in the present invention to sensors which essentially enable detection of nerve activity. Description will be made with reference to electrodes that detect electrical or pulse stimulation by an electrical probe, however it will be appreciated that chemical sensors may be utilised that detect an increased presence of a specific chemical compound that is associated with a change in nerve activity.

Referring to the exemplary embodiment, and in particular sensor 2 there is provided a support 10 on which is supported an electrode 12 indicated by a plurality of dashed lines. The electrode may be in a number of different forms, however in one embodiment a conductive ink is printed onto the support, which may be termed a substrate. The conductive ink beneficially incorporates silver and even more beneficially silver chloride which has properties that enable transmittal of a good signal therethrough and is un-reactive. The support or substrate 10 may comprise a polyester film in the order of 50 microns thickness. The conductive ink is then over printed with a lacquer material in areas in which an electrical signal does not want to be received, such as in the areas at the opposing ends 10a and 10b of the support 10 which when secured to the cannula form a band around the cannula. As described below, the present invention is arranged such that a signal is received from the strips 16.

As can be seen in the Figures, the support has a longitudinal length generally parallel to the longitudinal length of the tube or cannula when secured to the cannula. A plurality of strips 16 of the support or substrate 10 extend generally in this longitudinal length, parallel to the longitudinal length. The strips 16 are formed from slots, slits or openings 18 formed in the longitudinal length of the support 10. When the sensor 10 is therefore secured to the cannula as shown in FIG. 1, the strips 16 can billow outwardly as the strips themselves are not secured to the cannula. As the strips are formed of the support which comprises a flexible material, these strips are therefore also flexible. This is extremely beneficial as this means that when the cannula is inserted the strips flex and sit adjacent or against the cannula with little force applied meaning there is no damage to the surrounding environment. Furthermore, once located in the desired position (for example adjacent the vocal cords), the strips billow outwardly thus ensuring contact with the vocal cords irrespective of the orientation of the cannula.

The strips carry an electrically conductive strip beneficially in the form of a printed conductive ink. This conductive ink forms an electrode which contacts the vocal cords for example and is therefore able to sense an electrical impulse, which varies depending on how close the probe (not shown) is to for example the nerve. It is beneficial that each strip 16, or sufficient strips 16 to wrap around the cannula each include an electrode to ensure that monitoring is successful irrespective of the orientation of the cannula.

Figure 3:
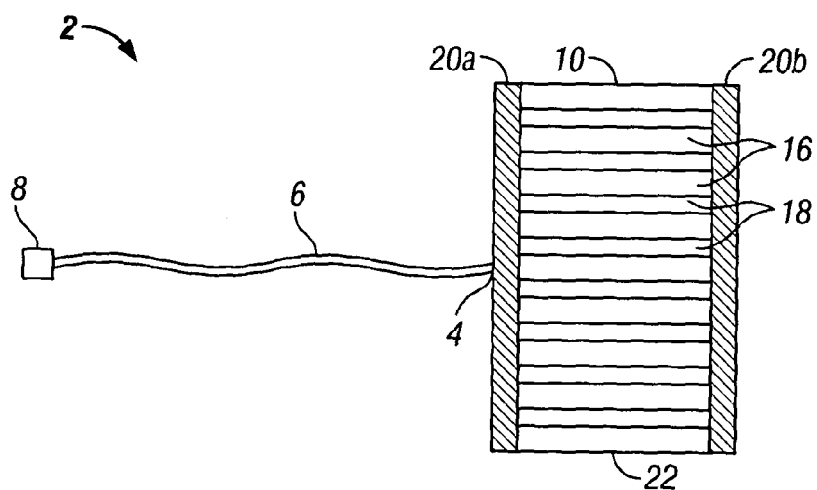
FIG. 3 is a schematic plan view of the lower or underside of a nerve sensing/monitoring sensor according to an exemplary embodiment of the present invention.

As briefly mentioned above, the sensor is wrapped around the cannula in a location as desired by the operator. Referring to FIG. 3, the underside of the sensor is shown again showing the strips 16 and the adjacent slots 18. Shown however in FIG. 3 is an adhesive band 20a and 20b at opposing ends 10a, 10b of the sensor 2, where each end 10a and 10b may be a first and second zone respectively. The adhesive may however be provided in spots, points, small strips etc, providing that each end/edge of the transverse width of the sensor 2 is secured. The beneficial effect of the present invention is in part achieved through the provision of means to secure the sensor at opposing ends in situ on the tube or in particular the cannula. In the embodiment indicated therefore, an adhesive band or strip is provided at each end of the sensor 2. The adhesive is provided such that the strips 16 are secured at their ends, but the intermediate portion of the strips are free to move as required in order to occupy the space in for example the laryngeal space ensuring contact of the electrodes with the target nerves. The adhesive used is medical grade adhesive and is beneficially double sided, meaning that it can be secured to the sensor 2 during manufacture. When supplied to the practitioner the sensor and filament 6 is removed from sterile packaging, the adhesive backing removed, and the sensor is then adhered to the cannula.

It will be appreciated that for the effectiveness of the present invention, it is necessary for a zone adjacent or at an end of a plurality of strips to be secured. This provides a very simple yet very effective sensor where the electrodes are able to move outwardly or transversely relative to the longitudinal length of the sensor 6 thereby ensuring the one or more electrodes at least contact the target nerve. The strips are sufficiently flexible to accommodate to their surroundings, whilst are also able to be pressed inwardly to be adjacent the underlying tube (cannula). The end zones of the strips are therefore substantially immovable when in use relative to the underlying tube.

In one embodiment, it is envisaged that a further adhesive may be provided along at least part of the longitudinal edge of the sensor generally indicated at reference numeral 22. This beneficial when a practitioner is positioning the sensor 2 on the cannula in that the adhesive in the transverse direction is adhered first to the cannula, the backing can be removed for the adhesive on the longitudinal edge to ensue that this edge does not release accidentally in use. It is beneficial that there is some overlap once the sensor is wrapped around the cannula thus ensuring complete 360 degree sensing capability.

Reference is now made to FIGS. 4*a-c*. In FIGS. 4*a-c* there is a preferred embodiment of the present invention. It should be noted that the filament 6 for wrapping around an insertion member such as a cannula as identified by reference numeral 2 has been represented significantly reduced in length for clarity in the schematic diagrams.

Referring to FIG. 4*a*, the underside of the sensor arrangement is shown which wraps around an insertion member so faces inwardly towards the insertion member. When the sensor arrangement is provided in a sterilised packing prior to use a backing material is provided which is removed prior to application onto the insertion member. This backing material is not been shown for clarity. Furthermore, one or more portions of adhesive material 22 may be provided on the filament 6 for securing to an insertion member.

The sensor arrangement comprises one or more tabs 24 which may be utilised by the medical practitioner to enable ease of positioning onto the insertion member. The support 10 as can be seen in FIGS. 4*a-c* but in particular with reference to FIG. 4*b* in this embodiment comprises an adhesive layer 26 which is the surface layer visible in FIG. 4*a*. It should be noted that the adhesive layer is transparent meaning that an overlapping portion 28 of the material 30 carrying the electrode is shown in FIG. 4*a* having been wrapped around an edge of the intermediate layer 32 of the support 10. Accordingly, the support 10 comprises a layered structure comprising the adhesive layer 26, the intermediate layer 32 and the material 30 which carries the electrode. In the embodiment shown the electrodes are printed onto the material 30 as previously described. A plurality of slits, slots or openings 18 are provided in the material 30 allowing the strips 16 of the material 30 to project outwardly when the sensor arrangement 2 is wrapped around an insertion member. The strips effectively project outwardly from the intermediate layer 32. The sensor arrangement 2 is wrapped around an insertion member by positioning the tabs 24 longitudinally spaced on an insertion member and drawing the opposing tabs 25 circumferentially around the insertion member such that the adhesive layer 26 adheres to the insertion member. In such a configuration the longitudinal length of a sensor arrangement 2 is fixed by the web portion 34 of the support 10. This means that the radial or outward expansion of the strips 16 clearly shown in FIG. 4*b* is fixed by the longitudinal length of the web portion meaning that the strips 16 can deflect as appropriate to conform to the anatomical geometry of an internal body space. The amount of outward or radial expansion of the strips is therefore not controlled by the medical practitioner applying the sensor arrangement to the insertion member, rather is fixed by the intermediate layer of the support and the length of the strips 16.

The distal end of the sensor arrangement as described with respect to the previous embodiment comprises an output element 8 comprising a plurality of electrical connections 38 and a connecting member 4 for securing to monitoring apparatus. The connection 4 is beneficially releasable.

Reference is made to FIG. 4*b*. The direction in which FIG. 4*a* is viewed is identified by the arrow and 'Y' in FIG. 4*a*. It should also be noted that the thicknesses of the respective layers of the support as shown in FIG. 4*b* are not to scale and are shown for explanation purposes only. The layered structure of the sensor arrangement is clearly shown.

Reference is now made to FIG. 4*c*. FIG. 4*c* is a plan view of the sensor arrangement 2 and shows the electrical connections and sensing elements printed onto the support 10. As previously described, the sensing elements are printed onto the strips 16 made from the material 30 which extends from the sensor arrangement along the filament 6 to the outward element 8. The surface presented in FIG. 4*c* includes the strips 16 separated by slits 18 where the strips 16 have been coated with electrically conductive material as described with respect to the first embodiment. A circuit can therefore be shown on each side of the support 10 identified by reference numerals 44 and 45.

The present invention has been described by way of example only and it will be appreciated to the skilled address that modifications and variations may be made to the present invention with departing from the scope of protection afforded by the appended claims.

The invention claimed is:

1. A sensor arrangement for sensing activity in a nerve or muscle, the sensor arrangement being arranged to be secured to an insertion member for insertion into a body cavity, the sensor arrangement comprising a support for supporting one or more sensing elements, the support comprising a first zone, a second zone, and an intermediate portion extending between the first and second zone arranged to space apart the second zone longitudinally from the first zone, where each of the first and second zones and intermediate portion are arranged to be secured to the insertion member to define a fixed spacing between the first and second zones, wherein a plurality of strips comprising one or more sensing elements bridge at least part of the spacing between the first and second zones, the strips being moveable laterally relative to the longitudinal length of the support.

2. The sensor arrangement according to claim 1, wherein the strips extending between the first and second zone are unsecured intermediate the first and second zones.

3. The sensor arrangement according to claim 1, wherein the support comprises the one or more strips for supporting the one or more sensing elements.

4. The sensor arrangement according to claim 1 further comprising a securing arrangement for securing the first zone and a securing arrangement for securing the second zone to the insertion member.

5. The sensor arrangement according to claim 4, wherein the securing arrangements comprise an adhesive.

6. The sensor arrangement according to claim 1, wherein the intermediate portion comprises a securing arrangement for securing the intermediate zone to an insertion member.

7. The sensor arrangement according to claim 1, wherein the sensing element comprises an electrode.

8. The sensor arrangement according to claim 7, wherein the electrode comprises a conductive ink.

9. The sensor arrangement according to claim 1, wherein the strips are flexible and are moveable radially outwardly from the insertion member when the sensor is secured to an insertion member.

10. The sensor arrangement according to claim 1, wherein the support is arranged to conform to the outer surface configuration of an insertion member.

11. The sensor arrangement according to claim 1, wherein the support comprises at least one tab element projecting generally transversely to the longitudinal length of the strips.

12. A sensor arrangement according to claim 1, wherein the sensor arrangement is a laryngeal sensor arrangement capable of insertion into the laryngeal cavity.

13. The sensor arrangement according to claim 1, wherein the strips are positioned in a side-by-side configuration.

14. The sensor arrangement according claim 1, wherein the strips are arranged to move independently of each other.

15. The sensor arrangement according to claim 1, wherein the strips extending between the first and second zone are unsecured intermediate the first and second zones; and
   wherein each of the first zone, second zone, and intermediate portion have an adhesive on them to fix to the insertion member.

16. An insertion member comprising an elongate body having a sensor arrangement according to claim 1 secured to the elongate body.

17. The insertion member according to claim 16, wherein the sensor arrangement is wrapped around the body.

18. The insertion member according to claim 16, wherein the insertion member is a cannula.

19. An insertion member according to claim 16, wherein the strips align substantially parallel to the longitudinal length of the elongate body.

\* \* \* \* \*